United States Patent [19]

Saville

[11] Plant 5,093

[45] Aug. 30, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 382,490

[22] Filed: May 27, 1982

[51] Int. Cl.[3] ..... A01H 5/00

[52] U.S. Cl. ..... Plt./7

[58] Field of Search ..... Plt./7

*Primary Examiner*—James R. Feyrer

*Attorney, Agent, or Firm*—Vincent G. Gioia

[57] ABSTRACT

A new red and yellow bicolor miniature rose variety.

1 Drawing Figure

The present invention relates to a new and distinct variety of rose plant of the hybrid tea rose class, which was originated by my crossing as seed parent my seedling of unknown parentage and the rose known as "Poker Chip" as pollen parent. The denomination of this new rose is "Savabean".

Among the novel characteristics possessed by this new variety which distinguish it from its parents and all other varieties of which I am aware are its red and yellow bicolored flowers with bright red petal top surface and aureolin yellow petal undersurface. The flowers have washing of red into yellow at the edges of the petal undersurface and the plant is vigorous but low growing. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "12D" is plate 12D of The Royal Horticultural Society Colour Chart.

Parentage: Seedling.

*Seed parent.*—My unpatented, unreleased seedling of unknown parentage.

*Pollen parent.*—"Poker Chip".

Class: Miniature.

The following observations are made of specimens grown under glass in Essex County, Mass. during the month of March.

FLOWER

Blooming habit: Recurrent to continuous.

A. Bud:

(1) *Size.*—Medium.

(2) *Form.*—Pointed, ovate.

(3) *Color.*—After sepals divide, visible undersurface appears as a blend of aureolin 12D and red 42A but some 42A coloring from petal top surface is also visible as is washing of red and aureolin toward petal edges. On the petal undersurface the red edge coloring varies from only at petal edge to extension somewhat into the petal from the edge.

(4) *Sepals.*—Slightly longer than bud.

(5) *Peduncle.*—Length — about 5/16 to $\frac{3}{8}$ inch. Aspect — straight. Strength — erect. Color — near 145B.

B. Bloom:

(1) *Size.*—Average size when fully expanded — about 1 to $1\frac{3}{8}$ inches.

(2) *Borne.*—Singly and small sprays.

(3) *Form.*—Ovoid buds become cup-shaped flowers, petals generally quilling.

(4) *Petalage.*—Number of petals under normal conditions — about 12 to 15.

(5) *Color.*—The flower appears essentially as a red and yellow bicolor. However, the yellow petal undersurface (aureolin 12D) tends to be washed, generally at petal edges, with red 42A. At point of petal attachment petals are deeper yellow. Petal top surface is substantially red 42A, except close to point of petal attachment, as aforesaid.

C. Petals:

(1) *Texture.*—Thick.

(2) *Appearance.*—Inside velvety, outside satiny.

(3) *Form.*—Fan shaped.

(4) *Arrangement.*—Regularly arranged, shingle-like.

(5) *Petaloids in center.*—Few.

(6) *Persistence.*—Drop off cleanly.

(7) *Fragrance.*—Slight, sweet.

(8) *Lasting quality.*—Good lasting quality on plant and as cut flower.

REPRODUCTIVE ORGANS

A. Stamens, filaments and anthers:

(1) *Arrangement.*—Stamens regularly arranged around styles.

(2) *Color.*—Near 20A.

B. Pollen:

*Color.*—Near 21B.

C. Styles: Even, medium length.

D. Stigmas:

*Color.*—Near 160D.

E. Hips: None observed.

PLANT

A. Form: Compact, bushy.

B. Growth: Vigorous.

*Height attained.*—About 10 inches.

C. Foliage: Compound 5 to 7 leaflets.

(1) *Size.*—Small.

(2) *Quantity.*—Abundant.

(3) *Color.*—New foliage: Upper side — near to 137D. Under side — near to 138B. Old foliage: Upper side — near 137A. Under side — near 138B.

(4) *Shape.*—Oval.

(5) *Texture.*—Upper side is glossy and under side is matte.

(6) *Edge.*—Serrated.

(7) *Serration.*—Fine, regular.

(8) *Leaf stem.*—Color — near to 182B. Under side — near 177B.

(9) *Stipules.*—Medium, smooth.

(10) *Resistance to disease.*—Blackspot — average. Mildew — average. Rust — average.

D. Wood:

(1) *New wood.*—Color — near 146D. Bark — smooth.

(2) *Old wood.*—Color — near 137B. Bark — smooth.

E. Thorns:

(1) *Thorns.*—Quantity (main stalk) — few. On laterals from stalk — few. Form — thin, downward slanting. Length — long. Color — near 182B. Position — scattered.

(2) *Prickles.*—None.

F. Winter hardiness: Needs winter protection in severe climate.

I claim:

1. A new and distinct variety of rose plant of the miniature rose class, substantially as shown and described, characterized particularly by red and yellow bicolored flowers borne on a vigorous, but low growing plant.

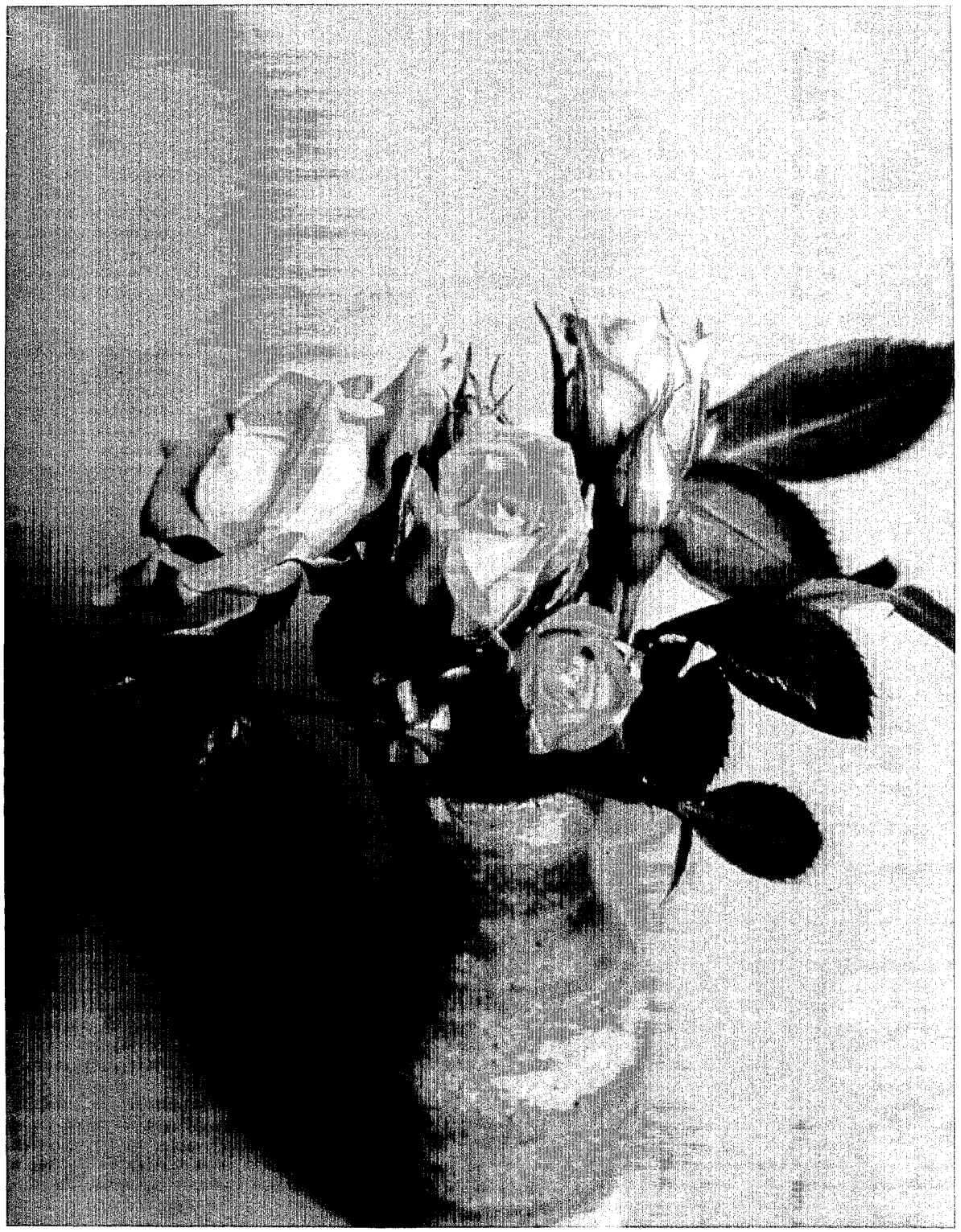

* * * * *